(12) United States Patent
Al-Saidi et al.

(10) Patent No.: US 8,591,557 B2
(45) Date of Patent: Nov. 26, 2013

(54) IMPLANT

(75) Inventors: Mohammad Dughaileeb Al-Saidi, Riyadh (SA); Nagwan Abo Alkhair, Riyadh (SA)

(73) Assignee: King Saud University, Riyadh (SA)

( * ) Notice: Subject to any disclaimer, the term of this patent is extended or adjusted under 35 U.S.C. 154(b) by 160 days.

(21) Appl. No.: 13/148,968

(22) PCT Filed: Feb. 12, 2010

(86) PCT No.: PCT/EP2010/000893
§ 371 (c)(1),
(2), (4) Date: Oct. 4, 2011

(87) PCT Pub. No.: WO2010/091881
PCT Pub. Date: Aug. 19, 2010

(65) Prior Publication Data
US 2012/0143259 A1    Jun. 7, 2012
US 2012/0330366 A2   Dec. 27, 2012

(30) Foreign Application Priority Data

Feb. 14, 2009    (SA) .................................. 109300110

(51) Int. Cl.
*A61B 17/80*    (2006.01)
(52) U.S. Cl.
USPC ......................................... 606/298; 606/331

(58) Field of Classification Search
USPC .......................................................... 606/298
See application file for complete search history.

(56) References Cited

U.S. PATENT DOCUMENTS

| 5,466,455 | A  | * | 11/1995 | Huffstutler et al. | ........... 424/401 |
| 7,090,668 | B1 | * | 8/2006  | U et al.           | ..................... 604/892.1 |
| 7,250,055 | B1 | * | 7/2007  | Vanderwalle        | ................... 606/92 |
| 8,092,841 | B2 | * | 1/2012  | Cohen              | ......................... 424/725 |

FOREIGN PATENT DOCUMENTS

| EP | 1 972 352 | 9/2008 |
| WO | 98/41547  | 9/1998 |

OTHER PUBLICATIONS

PCT/EP2010/000893; PCT International Search Report and Written Opinion of the International Searching Authority dated Nov. 30, 2010.

* cited by examiner

*Primary Examiner* — Nicholas Woodall
(74) *Attorney, Agent, or Firm* — Renner, Otto, Boisselle & Sklar, LLP

(57) ABSTRACT

The present invention relates to a implant for implantation into a body of an animal, wherein the implant comprises material of inner core of drupes and/or palm tree fruits.

16 Claims, No Drawings

IMPLANT

The present invention relates to an implant for implantation into a body of an animal and the use thereof.

It is known in the prior art to use metal or ceramic implants, such as screws, to stabilize bone fractures, the implants being implanted in surgical operations. Bones and fractures can be put into place by the implants, and they can promote adhesion of the fractured bone parts.

Conventional metal screws, made from chrome, titanium or specific steel compositions, are known which have to be implanted into the body. After a specific time, such conventional screws have usually to be removed from the body which is done by further surgical operations which causes additional pain and suffering to the patient and also requires further energy, money and time.

The hardness of the conventionally used implants can still be improved so that, for example, a less number of implants is necessary to stabilize a specific bone fracture.

Palmae, or palm trees, is a family of flowering plants and are among the best known and extensively cultivated plant families. They have been important to humans throughout much of history. Many common products and foods are derived from palms, and palms are also widely used in landscaping for their exotic appearance, making them one of the most economically important plants.

Date palm (*phoenix dactylifera*) is a palm extensively cultivated for its edible sweet fruit. Dates have been a staple food of the middle east for thousands of years. A drupe is a fruit in which an outer fleshy part (exocarp) surrounds a shell of hardened endocarp with a seed inside.

It is an object of the present invention to provide an implant for implantation into a body of an animal which overcomes the drawbacks of the prior art. Especially, an implant shall be provided which does not need to be removed from the body and shows improved hardness compared to the conventionally used implants.

This object is achieved by an implant for implantation into a body of an animal, wherein the implant comprises material of inner core of drupes and/or palm tree fruits.

Preferably, the drupes and/or fruits are selected from the group consisting of palm date, *hyphaena thebaica*, olive, peach, plum or cherry, preferably palm date.

Most preferably, the implant is in the form of a screw, nail or plate.

In one embodiment, the animal is a mammal, preferably a human being.

A further object is achieved by the use of the inventive implant for implanting into a body of an animal, preferably for stabilizing bone fractures.

Surprisingly, it was found according to the present invention that an implant comprising material of inner core of drupes and/or palm tree fruits as implant material overcomes the drawbacks of the prior art. Especially, it was found that there is no need to a further surgical operation to remove the implant as the implant according to the present invention dissolves over a reasonable time and turns into a jelly substance which is quite similar to the substance of bones. In contrast to that, conventional implants require an additional operation to remove the implant which of course causes more pain and suffering to the patients. The implant of the present invention also saves energy, money and time.

A further advantage of the inventive implant is the fact that the hardness of the implant is significantly improved. This allows the use of less implants than in the prior art to stabilize a specific bone fracture.

The inventive implant, for example a screw, can be fixed in and/or at the bone and holds the fractured parts motionless. The implant of the invention starts to dissolve after approximately half a month from the date of implantation, and after a time period of from six to nine months after operation the implant is substantially dissolved into a jelly substance. The jelly substance was analyzed and was found to contain proteins, carbohydrates, fats, fibers and mineral salts in an amount and composition which is quite comparable to the components of bones.

Additional features and advantages of the present invention can be taken from the following detailed description of preferred embodiments.

Preparation of an Implant from Date Palm Inner Core

The implant of the present invention can be prepared by any methods as known in the art. For example, the implant, for example a screw, can be sculptured. In an alternative, for example date palm inner core can be ground, and the particles obtained may then be glued together using, preferably, natural gluing agent extracted from plants. A sculptured implant is preferred.

Hardness of the Implant

The hardness of the screw, as prepared above, was measured on a torque measuring device, and many values of torque from 20 to 60 Newtons were applied, wherein the screw resisted up to 60 Newtons where it dethatched but did not break or fracture.

In an comparative example a conventional steel screw was tested. It was found that a conventional steel screw of the prior art already breaks at 30 Newtons.

Dissolution Tests of the Inventive Screw

1. A screw, as prepared above, was put into a sodium bicarbonate solution having a pH=7. The screw started to dissolve after 40 days and was substantially completely dissolved after eight months, where it turned into a jelly substance. The jelly substance was analyzed and the following ingredients were found (amounts in weight percent, based on the total weight of the screw):

23% proteins
62% carbohydrates
8% fats
1% fibers
5% mineral salts (iron, phosphor, potassium, sodium, magnesium).

2. A screw, as prepared above, was put in a model stomach juice solution having a pH=7. The screw started to dissolve after about a month and turned into a jelly substance after seven months. Again, the jelly substance was analyzed and revealed 23% protein, 62% carbohydrates, 8% fats, 1% fibers and 5% mineral salts (iron, phosphor, potassium, sodium, magnesium).

In Vivo-Implantation

A screw, as prepared above, was implanted into a six months old lamb, weighting 30 kg, and having a fractured hind leg. The screw was inserted in a sectional orientation and supported the leg and held the fractured bones in place. The leg was then splinted and the lamb was put under care for 3 weeks after which the splint was removed and the leg was examined. It was found that the fracture has been completely healed and no side effects were found in the area where the screw was implanted. The screw has stuck in the bone and has fused with the bone tissue. The lamb was able to walk flawlessly after having these checkups. It was further found that the screw started to dissolve after a duration of one month from the date of the operation, and by periodic examinations of the lamb's leg it was shown that no sepsis was found in the area it was implanted and did not pose any problems on the health of the lamb.

As illustrated above, a single screw was able to maintain the fractured area and withstand the lamb's weight (30 kg). In contrast to that, using conventional implants it was found that 3 to 4 screws were needed to uphold the fractured area in place. Transferred to human beings having a weight of about 100 kg, it is assumed that five or six conventional screws are necessary to hold the fracture, whereas in contrast to that only about three implant screws of the present invention are necessary for the same purposes.

As a big bonus of the present invention, the inventive implant dissolves over the time. Thus, it is not necessary to initiate a second operation to unscrew the screw which saves money, energy and, of course, reduces pain on patients.

The features disclosed in the forgoing description and in the claims may, both separately and in any combination thereof, be material for realizing the invention in diverse forms thereof.

The invention claimed is:

1. Implant for implantation into a body of an animal, wherein the implant comprises material of inner core of drupes and/or palm tree fruits, wherein the implant consists of sculptured inner core of drupes and/or palm tree fruits.

2. Implant according to claim 1, wherein the drupes and/or palm tree fruits are selected from the group consisting of palm date, *hyphaena thebaica*, olive, peach, plum or cherry.

3. Implant according to claim 1, wherein the implant is in the form of a screw, nail or plate.

4. Implant according to claim 1, wherein the animal is a mammal.

5. A method of treating an animal comprising implanting the implant according to claim 1 into the body of the animal.

6. A method according to claim 5 wherein the implant is implanted to stabilize a bone fracture.

7. Implant according to claim 1, wherein the drupes and/or palm tree fruits are palm date.

8. Implant according to claim 1, wherein the animal is a human being.

9. Implant for implantation into a body of an animal, wherein the implant comprises material of inner core of drupes and/or palm tree fruits, wherein the implant consists of ground particles of the inner core of drupes and/or palm tree fruits glued together using natural gluing agent extracted from plants.

10. Implant according to claim 9, wherein the drupes and/or palm tree fruits are selected from the group consisting of palm date, *hyphaena thebaica*, olive, peach, plum or cherry.

11. Implant according to claim 9, wherein the implant is in the form of a screw, nail or plate.

12. Implant according to claim 9, wherein the animal is a mammal.

13. A method of treating an animal comprising implanting the implant according to claim 9 into the body of the animal.

14. A method according to claim 13 wherein the implant is implanted to stabilize a bone fracture.

15. Implant according to claim 9, wherein the drupes and/or palm tree fruits are palm date.

16. Implant according to claim 9, wherein the animal is a human being.

* * * * *

UNITED STATES PATENT AND TRADEMARK OFFICE
CERTIFICATE OF CORRECTION

PATENT NO. : 8,591,557 B2  
APPLICATION NO. : 13/148968  
DATED : November 26, 2013  
INVENTOR(S) : Al-Saidi et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 210 days.

Signed and Sealed this
Twenty-second Day of September, 2015

Michelle K. Lee
*Director of the United States Patent and Trademark Office*